United States Patent
Pather et al.

(10) Patent No.: US 6,200,604 B1
(45) Date of Patent: Mar. 13, 2001

(54) SUBLINGUAL BUCCAL EFFERVESCENT

(75) Inventors: Sathasivan Indiran Pather, Plymouth; Rajendra K. Khankari, Maple Grove, both of MN (US); Jonathan D. Eichman, Ann Arbor, MI (US); Joseph R. Robinson, Madison, WI (US); John Hontz, Plymouth, MN (US)

(73) Assignee: Cima Labs Inc., Minneapolis, MN (US)

( * ) Notice: Subject to any disclaimer, the term of this patent is extended or adjusted under 35 U.S.C. 154(b) by 0 days.

(21) Appl. No.: 09/327,814

(22) Filed: Jun. 8, 1999

Related U.S. Application Data

(63) Continuation of application No. 09/277,424, filed on Mar. 26, 1999.
(60) Provisional application No. 60/079,652, filed on Mar. 27, 1998.

(51) Int. Cl.$^7$ ................................. A61K 9/46; A61K 9/20
(52) U.S. Cl. ........................... 424/466; 424/465; 424/434
(58) Field of Search ................................ 424/466, 465, 424/464, 435

(56) References Cited

U.S. PATENT DOCUMENTS

| | | | |
|---|---|---|---|
| 3,972,995 | * 8/1976 | Tsuk et al. | 424/28 |
| 4,493,848 | 1/1985 | LaHann et al. | 424/324 |
| 4,639,368 | 1/1987 | Niazi et al. | 424/48 |
| 5,135,752 | * 8/1992 | Snipes | 424/486 |
| 5,178,878 | * 1/1993 | Wehling et al. | 424/466 |
| 5,223,264 | * 6/1993 | Wehling et al. | 424/466 |
| 5,458,879 | 10/1995 | Singh et al. | 424/400 |
| 5,607,697 | 3/1997 | Alkire et al. | 424/495 |
| 5,656,284 | * 8/1997 | Balkin | 424/435 |
| 5,958,455 | * 9/1999 | Roser et al. | 424/489 |
| 5,958,468 | 9/1999 | Norling et al. | 424/490 |

FOREIGN PATENT DOCUMENTS

WO 91/04757   4/1991   (WO) .

OTHER PUBLICATIONS

Eichman, J.D., and Robinson, J.R., "Mechanistic Studies on Effervescent–Induced Permeability Enhancement," Pharm. Res. 15(6):925–30 (1998).
Squier, C.A., and Wertz, P.W., "Structure and Function of the Oral Mucosa and Implications for Drug Delivery", *Oral Mucosal Drug Delivery*, Ch. 1, pp. 1–19 (1996).
Wertz et al., "Biochemical Basis of the Permeability Barrier in Skin and Oral Mucosa", *Oral Mucosal Drug Delivery*, Ch. 2, pp. 27–41 (1996).
Zhang, H., and Robinson, J.R., "Routes of Drug Transport Across Oral Musoca", *Oral Mucosal Drug Delivery*, Ch. 3, pp. 51–61 (1996).
Aungst, B.J., "Oral Mucosal Permeation Enhancement: Possibilities and Limitations", *Oral Mucosal Drug Delivery*, Ch. 4, pp. 65–81 (1996).
Zhang, H., and Robinson, J.R., "In Vitro Methods for Measuring Permeability of the Oral Mucosa", *Oral Mucosal Drug Delivery*, Ch. 5, pp. 85–97 (1996).
Audus, K.L., "Buccal Epithelial Cell Cultures as a Model to Study Oral Mucosal Drug Transport and Metabolism", *Oral Mucosal Drug Delivery*, Ch. 6, pp. 101–115 (1996).
Rathbone et al., "In Vivo Techniques for Studying the Oral Mucosal Absorption Characteristics of Drugs in Animals and Humans", *Oral Mucosal Drug Delivery*, Ch. 7, pp. 121–151 (1996).
Weatherell et al., "The Flow of Saliva and Its Influence on the Movement, Deposition and Removal of Drugs Administered to the Oral Cavity", *Oral Mucosal Drug Delivery*, Ch. 8, pp. 157–187 (1996).
Schenkels et al., "Salivary Mucins: Their Role in Oral Mucosal Barrier Function and Drug Delivery", *Oral Mucosal Drug Delivery*, Ch. 9, pp. 191–211 (1996).
Kellaway, I.W., and Warren, S.J., "Mucoadhesive Hydrogels for Buccal Delivery", *Oral Mucosal Drug Delivery*, Ch. 10, pp. 221–237 (1996).
Rathbone et al., "Systemic Oral Mucosal Drug Delivery and Delivery Systems", *Oral Mucosal Drug Delivery*, Ch. 11, pp. 241–275 (1996).
DeGrande et al., "Specialized Oral Mucosal Durg Delivery Systems: Patches", *Oral Mucosal Drug Delivery*, Ch. 12, pp. 285–313 (1996).
Rassing, .R., "Specialized Oral Mucosal Drug Delivery Systems: Chewing Gum", *Oral Mucosal Drug Delivery*, Ch. 13, pp. 319–353 (1996).
Soskolone, W.A., and Freidman, M., "Intra–periodontal Pocket Drug Delivery Systems", *Oral Mucosal Drug Delivery*, Ch. 14, pp. 359–373 (1996).

\* cited by examiner

*Primary Examiner*—Thurman K. Page
*Assistant Examiner*—Isis Ghali
(74) *Attorney, Agent, or Firm*—Lerner, David, Littenberg, Krumholz & Mentlik, LLP

(57) ABSTRACT

A pharmaceutical dosage form adapted to supply a medicament to the oral cavity for buccal, sublingual or gingival absorption of the medicament which contains an orally administerable medicament in combination with an effervescent for use in promoting absorption of the medicament in the oral cavity. The use of an additional pH adjusting substance in combination with the effervescent for promoting the absorption drugs is also disclosed.

12 Claims, No Drawings

SUBLINGUAL BUCCAL EFFERVESCENT

CROSS-REFERENCE TO RELATED APPLICATIONS

The present application is a continuation application of U.S. patent application Ser. No. 09/277,424, filed Mar. 26, 1999.

The present invention claims the benefit of the U.S. Provisional Application Ser. No. 60/079,652 filed on Mar. 27, 1998, the disclosure of which is incorporated by reference herein.

BACKGROUND OF THE INVENTION

1. Field of the Invention

The present invention relates to pharmaceutical compositions, and more particularly to pharmaceutical compositions for oral administration of a medicament, which contain an effervescent agent for enhancing oral drug absorption across the buccal, sublingual, and gingival mucosa.

2. Description of Prior Art

Effervescents have been shown to be useful and advantageous for oral administration. See Pharmaceutical DosageForms: Tablets Volume I, Second Edition. A. Lieberman. ed. 1989, Marcel Dekker, Inc. As discussed in this text, and as commonly employed, an effervescent tablet is dissolved in water to provide a carbonated or sparkling liquid drink. See also U.S. Pat. Nos. 5,102,665 and 5,468,504 to Schaeffer, herein incorporated by reference. In such a drink, the effervescent helps to mask the taste of medicaments.

Effervescent compositions have also been employed for use as taste masking agents in dosage forms which are not dissolved in water prior to administration. For example, U.S. Pat. No. 4,639,368 describes a chewing gum containing a medicament capable of absorption through the buccal cavity and containing a taste masking amount of an effervescent.

More recently effervescents have been employed to obtain rapid dissolution and/or dispersion of the medicament in the oral cavity. See U.S. Pat. Nos. 5,178,878 and 5,223,264. The effervescent tends to stimulate saliva production thereby providing additional water to aid in further effervescent action. These dosage forms give an agreeable presentation of the drug, particularly for patients who have difficulty in swallowing tablets or capsules. PCT application WO 97/06786 describes pre-gastric absorption of certain drugs using rapidly-disbursing dosage forms.

Various proposals have been advanced for oral mucosal administration of various drugs. When drugs are absorbed from the oral mucosa, they bypass the gastrointestinal and hepatic metabolism process. This can lead to a faster onset of action and/or improved bioavailability of a drug. However, many compounds do not rapidly penetrate the oral mucosa. See, e.g., Christina Graffner, *Clinical Experience with Novel Buccal and Sublingual Administration;* NOVEL DRUG DELIVERY AND ITS THERAPEUTIC APPLICATION, edited by L. F. Prescott and W. S. Nimmo (1989); David Harris & Joseph R. Robinson, *Drug Delivery via the Mucous Membranes of the Oral Cavity;* JOURNAL OF PHARMACEUTICAL SCIENCES, Vol. 81 (January 1992); *Oral Mucosal Delivery,* edited by M. J. Rathbone, which are herein incorporated by reference. The compounds which may be well absorbed per-orally (through the gastrointestinal tract) may not be well absorbed through the mucosa of the mouth because the oral mucosa is less permeable than the intestinal mucosa and it does not offer as big a surface area as the small intestine.

Despite these and other efforts toward increasing the permeation of medicaments across the oral mucosa, there have been unmet needs for improved methods of administrating medicaments across the oral mucosa.

SUMMARY OF THE INVENTION

The pharmaceutical compositions of the present invention comprise an orally administerable medicament in combination with an effervescent agent used as penetration enhancer to influence the permeability of the medicament across the buccal, sublingual, and gingival mucosa.

DETAILED DESCRIPTION OF THE INVENTION

One aspect of this invention is to use effervescent as penetration enhancers for influencing oral drug absorption. Effervescent agents can be used alone or in combination with other penetration enhancers, which leads to an increase in the rate and extent of absorption of an active drug. It is believed that such increase can rise from one or all of the following mechanisms:

1. reducing the mucosal layer thickness and/or viscosity;
2. tight junction alteration;
3. inducing a change in the cell membrane structure; and
4. increasing the hydrophobic environment within the cellular membrane.

The present dosage forms should include an amount of an effervescent agent effective to aid in penetration of the drug across the oral mucosa. Preferably, the effervescent is provided in an amount of between about 5% and about 95% by weight, based on the weight of the finished tablet, and more preferably in an amount of between about 30% and about 80% by weight. It is particularly preferred that sufficient effervescent material be provided such that the evolved gas is more than about 5 $cm^3$ but less than about 30 $cm^3$, upon exposure of the tablet to an aqueous environment. However, the amount of effervescent agent must be optimized for each specific drug.

The term "effervescent agent" includes compounds which evolve gas. The preferred effervescent agents evolve gas by means of a chemical reaction which takes place upon exposure of the effervescent agent (an effervescent couple) to water and/or to saliva in the mouth. This reaction is most often the result of the reaction of a soluble acid source and a source of carbon dioxide such as an alkaline carbonate or bicarbonate. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

The effervescent agent(s) of the present invention is not always based upon a reaction which forms carbon dioxide. Reactants which evolve oxygen or other gasses which are safe for human consumption are also considered within the scope. Where the effervescent agent includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

The present dosage forms may also include in amounts additional to that required for effervescence a pH adjusting substance. For drugs that are weakly acidic or weakly basic, the pH of the aqueous environment can influence the relative concentrations of the ionized and unionized forms of the drug present in solution according to the Henderson-Hasselbach equation. The pH solutions in which an effervescent couple has dissolved is slightly acidic due to the evolution of carbon dioxide. The pH of the local environment, e.g., saliva in immediate contact with the tablet and any drug that may have dissolved from it, may be adjusted by incorporating in the tablet a pH adjusting substances which permit the relative portions of the ionized and unionized forms of the drug to be controlled. In this way, the present dosage forms can be optimized for each specific drug. If the unionized drug is known or suspected to be absorbed through the cell membrane (transcellular absorption) it would be preferable to alter the pH of the local environment (within the limits tolerable to the subject) to a level that favors the unionized form of the drug. Conversely, if the ionized form is more readily dissolved the local environment should favor ionization.

The aqueous solubility of the drug should preferably not be compromised by the effervescent and pH adjusting substance, such that the dosage forms permit a sufficient concentration of the drug to be present in the unionized form. The percentage of the pH adjusting substance and/or effervescent should therefore be adjusted depending on the drug.

Suitable pH adjusting substance for use in the present invention include any weak acid or weak base in amounts additional to that required for the effervescence or, preferably, any buffer system that is not harmful to the oral mucosa. Suitable pH adjusting substance for use in the present invention include, but are not limited to, any of the acids or bases previously mentioned as effervescent compounds, disodium hydrogen phosphate, sodium dihydrogen phosphate and the equivalent potassium salt.

The active ingredient suitable for use in the present dosage forms can include systematically distributable pharmaceutical ingredients, vitamins, minerals, dietary supplements, as well as non-systematically distributable drugs. Preferably, the active ingredient is a systemically active pharmaceutical ingredient which is absorbable by the body through the oral mucosa. Although the dosage forms can be employed with a wide range of drugs, as discussed below, it is especially suitable for drugs and other pharmaceutical ingredients which suffer significant loss of activity in the lumen of the gastrointestinal tract or in the tissues of the gastrointestinal tract during absorption process or upon passage through the liver after absorption in the intestinal tract. Absorption through the oral mucosa allows the drug to enter the systemic circulation without first passing through the liver, and thus alleviates the loss of activity upon passage through the liver.

Pharmaceutical ingredients may include, without limitation, analgesics, anti-inflammatories, antipyretics, antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers; peptides, proteins, oligonucleotides and other substances of biological origin, and combinations thereof. Also encompassed by the terms "active ingredient(s)", "pharmaceutical ingredient(s)" and "active agents" are the drugs and pharmaceutically active ingredients described in Mantelle, U.S. Pat. No. 5,234,957, in columns 18 through 21. That text of Mantelle is hereby incorporated by reference. Alternatively or additionally, the active ingredient can include drugs and other pharmaceutical ingredients, vitamins, minerals and dietary supplements as the same are defined in U.S. Pat. No. 5,178,878, the disclosure of which is also incorporated by reference herein.

The dosage form preferably includes an effervescent couple, in combination with the other ingredients to enhance the absorption of the pharmaceutical ingredient across the oral mucosa and to improve the disintegration profile and the organoleptic properties of the dosage form. For example, the area of contact between the dosage form and the oral mucosa, and the residence time of the dosage form in the oral cavity can be improved by including a bioadhesive polymer in this drug delivery system. See, e.g., *Mechanistic Studies on Effervescent-Induced Permeability Enhancement* by Jonathan Eichman (1997), which is incorporated by reference herein. Effervescence, due to its mucus stripping properties, would also enhance the residence time of the bioadhesive, thereby increasing the residence time for the drug absorption. Non-limiting examples of bioadhesives used in the present invention include, for example, Carbopol 934 P, Na CMC, Methocel, Polycarbophil (Noveon AA-1), HPMC, Na alginate, Na Hyaluronate and other natural or synthetic bioadhesives.

In addition to the effervescence-producing agents, a dosage form according to the present invention may also include suitable non-effervescent disintegration agents. Non-limiting examples of non-effervescent disintegration agents include: microcrystalline, cellulose, croscarmelose sodium, crospovidone, starches, corn starch, potato starch and modified starches thereof, sweeteners, clays, such as bentonite, alginates, gums such as agar, guar, locust bean, karaya, pecitin and tragacanth. Disintegrants may comprise up to about 20 weight percent and preferably between about 2 and about 10% of the total weight of the composition.

In addition to the particles in accordance with the present invention, the dosage forms may also include glidants, lubricants, binders, sweeteners, flavoring and coloring components. Any conventional sweetener or flavoring component may be used. Combinations of sweeteners, flavoring components, or sweeteners and flavoring components may likewise be used.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Coloring agents may include titanium dioxide, and dyes suitable for food such as those known as F.D.& C. dyes and natural coloring agents such as grape skin extract, beet red powder, beta-carotene, annato, carmine, turmeric, paprika, etc. The amount of coloring used may range from about 0.1 to about 3.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.05 to about 3 percent by weight based upon the weight of the composition. Particularly preferred flavors are the grape and cherry flavors and citrus flavors such as orange.

One aspect of the invention provides a solid, oral tablet dosage form suitable for sublingual, buccal, and gingival administration. Excipient fillers can be used to facilitate tableting. The filler desirably will also assist in the rapid dissolution of the dosage form in the mouth. Non-limiting examples of suitable fillers include: mannitol, dextrose, lactose, sucrose, and calcium carbonate.

METHOD OF MANUFACTURE

Tablets can either be manufactured by direct compression, wet granulation or any other tablet manufacturing technique. See, e.g., U.S. Pat. Nos. 5,178,878 and 5,223,264, which are incorporated by reference herein. The tablet may be a layered tablet consisting of a layer of the active ingredient sandwiched between a bioadhesive layer and an effervescence layer. Other layered forms which include the ingredients set forth above in layers of diverse compositions.

| | |
|---|---|
| Effervescence Level | Between 5%–95% |
| Tablet size | Between ³⁄₁₆"–⅝" |
| Tablet hardness | Between 5N and 80N |
| Route of administration | Sublingual, Buccal, Gingival |

The dosage form may be administered to a human or other mammalian subject by placing the dosage form in the subject's mouth and holding it in the mouth, either adjacent a cheek (for buccal administration), beneath the tongue (for sublingual administration) and between the upper lip and gum (for gingival administration). The dosage form spontaneously begins to disintegrate due to the moisture in the mouth. The disintegration, and particularly the effervescence, stimulates additional salivation which further enhances disintegration.

EXAMPLE 1

The dosage form should include Fentanyl, an effervescent and pH adjusting substance so that the pH is adjusted to neutral (or slightly higher) since the pKa of fentanyl is 7.3. At this pH, the aqueous solubility of this poorly water-soluble drug would not be compromised unduly, and would permit a sufficient concentration of the drug to be present in the unionized form.

Two fentanyl formulations, each containing 36% effervescence were produced. These tablets were compressed using half-inch shallow concave punches.

| FORMULATION | COMPONENT | QUANTITY (MG) |
|---|---|---|
| SHORT DISINTEGRATION TIME | Fentanyl, citrate, USP | 1.57 |
| | Lactose monohydrate | 119.47 |
| | Microcrystalline Cellulose, Silicified | 119.47 |
| | Sodium carbonate, anhydrous | 46.99 |
| | Sodium bicarbonate | 105 |
| | Citric acid, anhydrous | 75 |
| | Polyvinylphrrolidone, cross-linked | 25 |
| | Magnesium stearate | 5 |
| | Colloidal silicon dioxide | 2.5 |
| | Total tablet mass | 500 |
| LONG DISINTEGRATION TIME | Fentanyl citrate, USP | 1.57 |
| | Lactose monohydrate | 270.93 |
| | Sodium carbonate, anhydrous | 40.00 |
| | Sodium bicarbonate | 105 |
| | Citric acid, anhydrous | 75 |
| | Magnesium stearate | 5 |
| | Colloidal silicon dioxide | 2.5 |
| | Total tablet mass | 500 |

EXAMPLE 2

The dosage form included prochlorperazine (pKa=8.1), an effervescent and pH adjusting substance so that a slightly higher pH is produced to facilitate the permeation enhancement.

With respect to prochlorperazine, an anti-emetic drug, two formulations, buccal and sublingual, were developed. The buccal tablets were compressed as quarter inch diameter biconvex tablets, whereas the sublingual tablets were three-eighths inch diameter biconvex tablets. These dimensions were chosen to give a comfortable fit in the respective part of the oral cavity for which they were designed. The formulae for these tablets are as follows:

| FORMULATION | COMPONENT NAME | QUANTITY (MG) |
|---|---|---|
| BUCCAL | Prochlorperazine | 5.00 |
| | Sodium Bicarbonate | 15.52 |
| | Citric Acid, Anhydrous | 11.08 |
| | Sodium Bicarbonate | 45.78 |
| | HPMC K4M Prem | 5.00 |
| | Dicalcium phosphate dihydrate | 5.00 |
| | Mannitol | 11.67 |
| | Magnesium Stearate | 0.95 |
| | Total | 100.00 |
| SUBLINGUAL | Prochlorperazine | 5.00 |
| | Sodium Bicarbonate | 61.25 |
| | Citric Acid, Anhydrous | 43.75 |
| | Sodium Bicarbonate | 95 |
| | Sodium carbonate | 91.25 |
| | HPMC Methocel K4M Prem | 40 |

-continued

| FORMULATION | COMPONENT NAME | QUANTITY (MG) |
|---|---|---|
| | Mannitol | 60 |
| | Magnesium Stearate | 3.75 |
| | Total | 400 |

What is claimed is:

1. A method of administering at least one systemically distributable pharmaceutical agent across the oral mucosa comprising:
   a) providing a solid oral dosage form including a pharmaceutically effective amount of an orally administerable medicament; and at least one effervescent agent in an amount sufficient to increase absorption of said orally administerable medicament across the oral mucosa; wherein said orally administerable medicament is not substantially encompassed by or dispersed in a material that prevents absorption of said medicament across the oral mucosa;
   b) placing said solid oral dosage form in the mouth of a patient so that saliva in said patient's mouth activates said at leant one effervescent agent in said tablet; and
   c) holding said solid oral dosage form and the dissolving contents of said solid oral dosage form it the mouth of a patient whereby said at least one effervescent agent promotes absorption of said orally administerable medicament across the oral mucosa.

2. The method of administering at least one systemically distributable pharmaceutical agent according to claim 1 wherein said solid oral dosage form further includes at least one pH adjusting substance.

3. The method of administering at least one systemically distributable pharmaceutical agent according to claim 1 or 2 wherein said step c) includes holding said solid oral dosage form and the dissolving contents of said solid oral dosage form in said mouth adjacent a cheek for buccal administration.

4. The method of administering at least one systemically distributable pharmaceutical agent according to claim 1 or 2 wherein said step c) includes holding said solid oral dosage form and the dissolving contents of said solid oral dosage form in said mouth beneath the tongue for sublingual administration.

5. The method of administering at least one systemically distributable pharmaceutical agent according to claim or 1 or 2 wherein said stop c) includes holding said solid oral dosage form and the dissolving contents of said solid oral dosage form in said mouth between the upper lip and gum for gingival administration.

6. The method of administering at least one systemically distributable pharmaceutical agent according to claim 1 or 2, wherein said solid oral dosage form further includes a bioadhesive, wherein said bioadhesive increases the contact time between said solid oral dosage form and the oral mucosa.

7. The method of administering at least one systemically distributable pharmaceutical agent according to claim 1 or 2, wherein said solid oral dosage form further includes glidants, lubricants, binders, sweeteners, flavoring and coloring components.

8. The method of administering at least one systemically distributable pharmaceutical agent according to claim 1 or 2, wherein said orally administerable medicament is selected from the group consisting of analgesics, anti-inflammatories, antipyretics, antibiotics, antimicrobials, laxatives, anorexics, antihistamines, antiasthmatics, antidiuretics, antiflatuents, anti-emtics, antimigraine agents, antispasmodics, sedatives, antihyperactives, antihypertensives, tranquilizers, decongestants, and beta blockers.

9. The method of administering at least one systemically distributable pharmaceutical agent according to claim 1 or 2, wherein said orally administerable medicament is selected from the group consisting of peptides, proteins and oligonucleotides.

10. The method of administering at least one systemically distributable pharmaceutical agent according to claim 1 or 2, wherein said at least one effervescent agent is present in an amount between about 5% by weight and 95% by weight.

11. The method of administering at least one systemically distributable pharmaceutical agent according to claim 1 or 2, wherein said at least one effervescent agent is present in an amount between about 30% by weight and 80% by weight.

12. The method of administering at least one systemically distributable pharmaceutical agent according to claim 1 or 2, wherein said at least one effervescent agent is present in an amount sufficient to evolve a gas in an amount between about 5 cm to about 30 cm.

* * * * *

UNITED STATES PATENT AND TRADEMARK OFFICE
CERTIFICATE OF CORRECTION

PATENT NO. : 6,200,604 B1
DATED : March 13, 2001
INVENTOR(S) : Pather et al.

It is certified that error appears in the above-identified patent and that said Letters Patent is hereby corrected as shown below:

Column 6,
Line 19, insert "dioxide"
Line 20, cancel "dioxide"
Line 28, insert "dioxide"
Line 29, cancel "dioxide"

Column 7,
Line 26, "leant" should read -- least --.

Column 8,
Line 2, cancel "or".
Line 3, "stop" should read -- step --.

Signed and Sealed this

Sixteenth Day of October, 2001

*Attest:*

NICHOLAS P. GODICI
*Attesting Officer*     Acting Director of the United States Patent and Trademark Office

UNITED STATES PATENT AND TRADEMARK OFFICE
CERTIFICATE OF CORRECTION

PATENT NO.    : 6,200,604 B1
DATED         : March 13, 2001
INVENTOR(S)   : S. Indiran Pather et al.

It is certified that error appears in the above-identified patent and that said Letters Patent is hereby corrected as shown below:

Column 7,
Line 28, "it" should read -- in --.

Column 8,
Line 2, "claim or 1 or" should read -- claim 1 or --.

Signed and Sealed this

Eighteenth Day of October, 2005

JON W. DUDAS
*Director of the United States Patent and Trademark Office*